US012667297B2

(12) United States Patent (10) Patent No.: US 12,667,297 B2

Tabata (45) Date of Patent: Jun. 30, 2026

(54) ELECTROCARDIOGRAPHIC DATA DETECTION APPARATUS AND METHOD

(71) Applicant: ALPS ALPINE CO., LTD., Tokyo (JP)

(72) Inventor: Masashi Tabata, Miyagi (JP)

(73) Assignee: ALPS ALPINE CO., LTD., Tokyo (JP)

( * ) Notice: Subject to any disclaimer, the term of this patent is extended or adjusted under 35 U.S.C. 154(b) by 195 days.

(21) Appl. No.: 18/737,082

(22) Filed: Jun. 7, 2024

(65) Prior Publication Data

US 2025/0017510 A1 Jan. 16, 2025

(30) Foreign Application Priority Data

Jul. 14, 2023 (JP) .................................. 2023-115690

(51) Int. Cl.
A61B 5/282 (2021.01)
A61B 5/00 (2006.01)
A61B 5/352 (2021.01)

(52) U.S. Cl.
CPC .............. A61B 5/352 (2021.01); A61B 5/282 (2021.01); A61B 5/6893 (2013.01)

(58) Field of Classification Search
CPC ....... A61B 5/30; A61B 5/0031; A61B 5/0245; A61B 5/18; A61B 5/282; A61B 5/283;

A61B 5/287; A61B 5/305; A61B 5/308; A61B 5/333; A61B 5/339; A61B 5/341; A61B 5/352; A61B 5/686; A61B 5/6893; A61B 5/7203

See application file for complete search history.

(56) References Cited

U.S. PATENT DOCUMENTS

2011/0125002 A1* 5/2011 Ershov ..................... A61B 5/18
600/384
2017/0224243 A1* 8/2017 Katra ..................... A61B 5/287

FOREIGN PATENT DOCUMENTS

JP 2007-082938 4/2007

* cited by examiner

*Primary Examiner* — Jon Eric C Morales
(74) *Attorney, Agent, or Firm* — IPUSA, PLLC

(57) ABSTRACT

An electrocardiographic data detection apparatus includes multiple electrodes disposed to face a human body; a difference signal generator configured to generate multiple difference signals from multiple sets of the multiple electrodes that are each a set of two electrodes of the multiple electrodes, each of the multiple difference signals being generated from signals of the two electrodes of the multiple electrodes; and a difference signal selector configured to select multiple difference signals suitable for measurement of a heartbeat from among the multiple difference signals generated by the difference signal generator.

11 Claims, 4 Drawing Sheets

| | ELECTRODE 1 | ELECTRODE 2 | ELECTRODE 3 | ELECTRODE 4 | ELECTRODE 5 | ELECTRODE 6 | ELECTRODE 7 | ELECTRODE 8 |
|---|---|---|---|---|---|---|---|---|
| ELECTRODE 1 | | 3.4 | 2.5 | 2.2 | 4.1 | 1.4 | 5.6 | 3.7 |
| ELECTRODE 2 | | | 4.1 | 2.1 | 4.6 | 2.2 | 5.4 | 4.3 |
| ELECTRODE 3 | | | | 4.1 | 2.5 | 2.3 | 3.6 | 2.4 |
| ELECTRODE 4 | | | | | 4.2 | 1.7 | 5.3 | 4.0 |
| ELECTRODE 5 | | | | | | 3.3 | 2.1 | 2.6 |
| ELECTRODE 6 | | | | | | | 3.5 | 2.1 |
| ELECTRODE 7 | | | | | | | | 3.7 |
| ELECTRODE 8 | | | | | | | | |

FIG.3

| | ELECTRODE 1 | ELECTRODE 2 | ELECTRODE 3 | ELECTRODE 4 | ELECTRODE 5 | ELECTRODE 6 | ELECTRODE 7 | ELECTRODE 8 |
|---|---|---|---|---|---|---|---|---|
| ELECTRODE 1 | | 3.3 | 2.6 | 2.3 | 4.2 | 1.4 | 2.4 | 3.4 |
| ELECTRODE 2 | | | 3.9 | 2.4 | 4.7 | 2.2 | 2.7 | 4.8 |
| ELECTRODE 3 | | | | 4.0 | 2.7 | 2.3 | 1.9 | 2.2 |
| ELECTRODE 4 | | | | | 4.3 | 1.7 | 2.4 | 3.9 |
| ELECTRODE 5 | | | | | | 3.2 | 1.7 | 2.7 |
| ELECTRODE 6 | | | | | | | 2.2 | 2.0 |
| ELECTRODE 7 | | | | | | | | 2.3 |
| ELECTRODE 8 | | | | | | | | |

ELECTROCARDIOGRAPHIC DATA DETECTION APPARATUS AND METHOD

CROSS-REFERENCE TO RELATED APPLICATIONS

The present application is based on and claims priority to Japanese Patent Application No. 2023-115690 filed on Jul. 14, 2023, the entire contents of which are hereby incorporated by reference.

BACKGROUND

1. Field of the Invention

The present disclosure relates to electrocardiographic data detection apparatuses and methods.

2. Description of the Related Art

Electrocardiographic measurement apparatuses including a pair of measurement insulating electrodes, and a measurement circuit are known. In these known electrocardiographic measurement apparatuses, the pair of measurement insulating electrodes are to be disposed to face a human body in a state of being electrically insulated, and the measurement circuit is configured to detect change in voltage caused through capacitance coupling between each of the measurement insulating electrodes and the human body, amplify the difference between two voltages detected by both of the measurement insulating electrodes, and provide an output as an electrocardiographic waveform signal. See, for example, Japanese Laid-Open Patent Application No. 2007-082938.

SUMMARY

An electrocardiographic data detection apparatus according to an embodiment of the present disclosure includes: multiple electrodes disposed to face a human body; a difference signal generator configured to generate multiple difference signals from multiple sets of the multiple electrodes that are each a set of two electrodes of the multiple electrodes, each of the multiple difference signals being generated from signals of the two electrodes of the multiple electrodes; and a difference signal selector configured to select multiple difference signals suitable for measurement of a heartbeat from among the multiple difference signals generated by the difference signal generator. The difference signal selector is configured to select a first difference signal and a second difference signal. The first difference signal is optimum for measurement of the heartbeat among the multiple difference signals generated by the difference signal generator. The second difference signal is optimum for measurement of the heartbeat among the multiple difference signals generated from signals of the multiple electrodes remaining by excluding, from the multiple electrodes, a pair of first electrodes that output original signals of the first difference signal.

BRIEF DESCRIPTION OF THE DRAWINGS

FIG. 1 is a diagram illustrating an example of a configuration of an electrocardiographic data detection apparatus of an embodiment;

FIG. 2 is a chart illustrating an example of signal-to-noise (SN) ratios of 28 difference signals obtained from eight electrodes;

2

Figure 4:
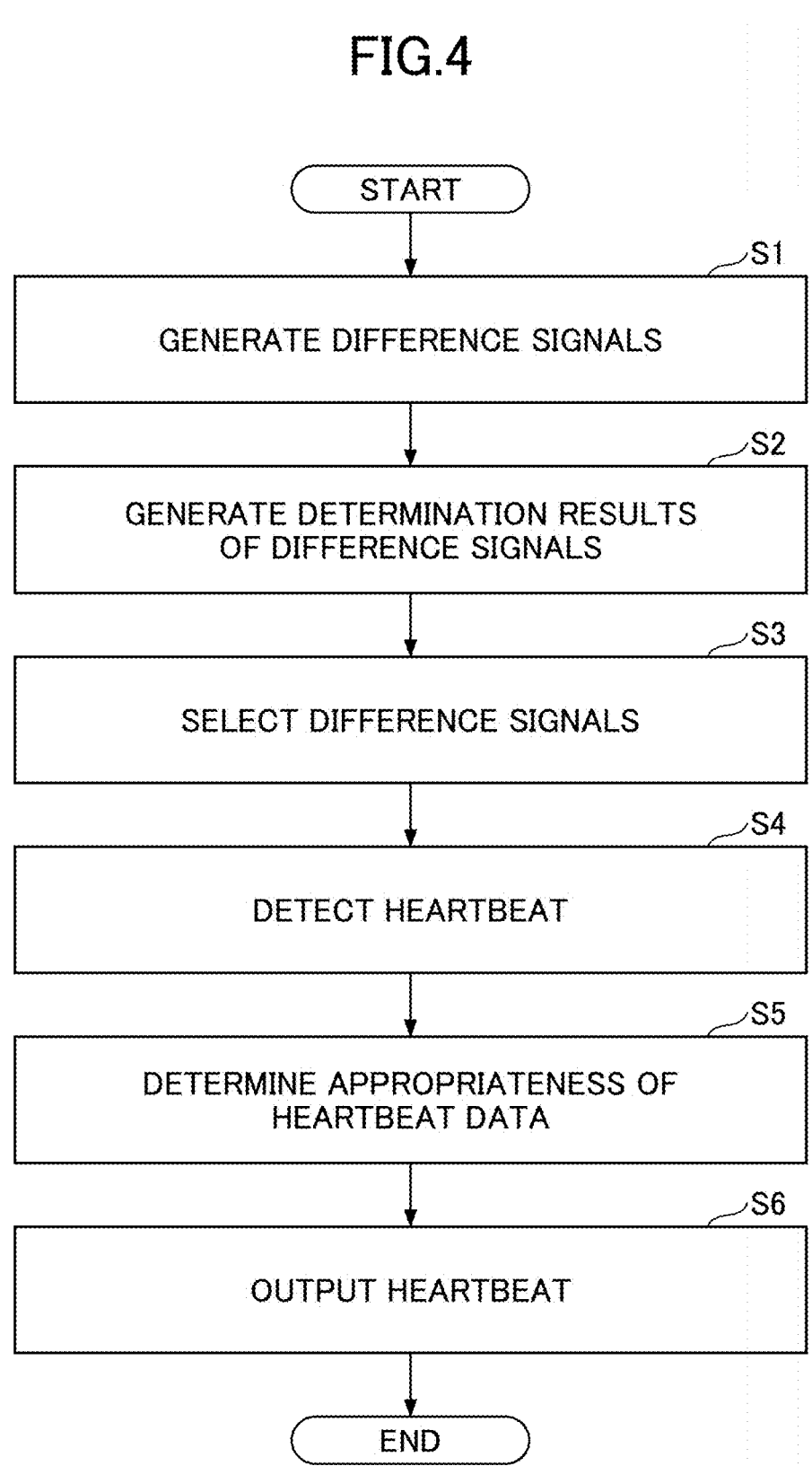

FIG. 3 is a chart illustrating an example of SN ratios of 28 difference signals obtained from eight electrodes; and FIG. 4 is a flowchart illustrating an example of a process executed by a micro controller unit (MCU) of the electrocardiographic data detection apparatus of the embodiment.

DETAILED DESCRIPTION OF THE INVENTION

Existing electrocardiographic measurement apparatuses include two measurement insulating electrodes and measure an electrocardiogram in accordance with a difference (difference signal) between voltages of the two measurement insulating electrodes. However, they do not obtain multiple difference signals using a larger number of electrodes and select a difference signal suitable for measurement of an electrocardiogram from among the multiple difference signals.

In view of the above, the present disclosure provides electrocardiographic data detection apparatus and method that can select difference signals suitable for detection of electrocardiographic data from among multiple difference signals.

Hereinafter, embodiments in which the electrocardiographic data detection apparatus and method of the present disclosure are applied will be described.

EMBODIMENTS

Figure 1:
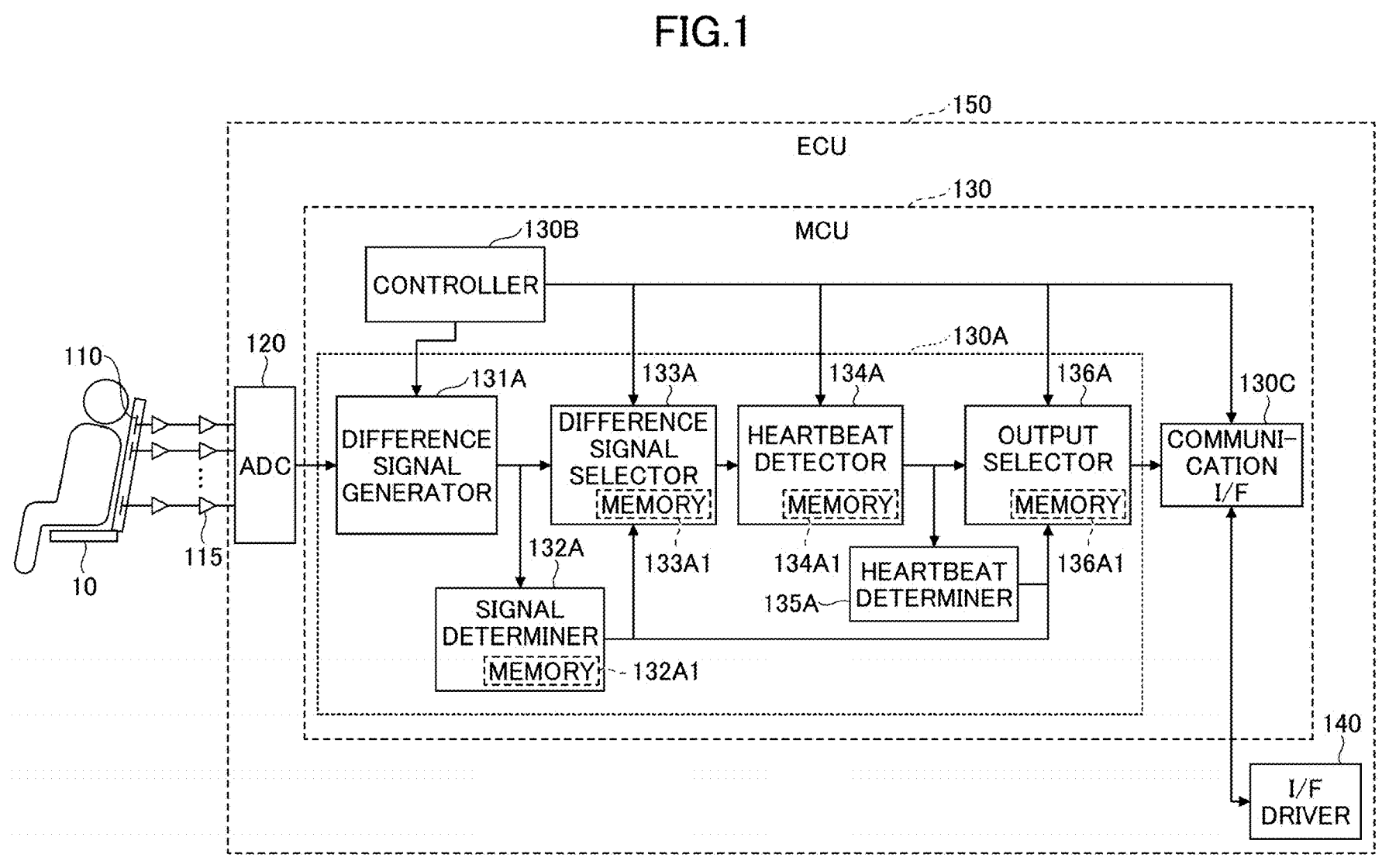

FIG. 1 is a diagram illustrating an example of a configuration of an electrocardiographic data detection apparatus 100 of an embodiment. The electrocardiographic data detection apparatus 100 includes multiple electrodes 110, a buffer circuit 115, an analog-to-digital convertor (ADC) 120, a micro controller unit (MCU) 130 (an example of a processor), and an interface (I/F) driver 140. The ADC 120, the MCU 130, and the I/F driver 140 form an electronic control unit (ECU) 150. The ECU 150 is mounted in a vehicle that one mounting example, and is connected to a high-level device via an on-board network that is one connection example.

The electrocardiographic data detected by the electrocardiographic data detection apparatus 100 is data indicating electrical activities of the heart. The electrocardiographic data encompasses: data including electrocardiographic waveforms and the like; and heartbeat data representing the heartbeat (R-R intervals, and heart rates obtained by R-R intervals) obtained on the basis of the electrocardiographic data. In the present embodiment, an example of determining the R-R intervals will be described.

As an example, the electrocardiographic data detection apparatus 100 is an apparatus configured to detect the electrocardiographic data of a driver who sits on a seat 10 of a driver's cab of a vehicle. FIG. 1 illustrates the seat 10 of the driver's cab of the vehicle. However, the electrocardiographic data detection apparatus 100 may be an apparatus configured to detect the electrocardiographic data of a passenger other than the driver who sits on the seat 10 of the driver's cab of the vehicle. In addition to the vehicle, the electrocardiographic data detection apparatus 100 may be applied to a chair disposed in a conference room, a chair disposed in a movie theater, and the like.

The multiple electrodes 110 are provided in the interior of the seat 10 of the driver's cab of the vehicle. More specifically, the multiple electrodes 110 are provided on the rear side of the outermost layer of the seating surface or backrest of the seat 10, and face the buttocks and the back of the driver sitting on the seat 10. As an example, a configuration in which eight electrodes 110 are provided in the seat 10 will be described. However, the number of the electrodes 110 is not limited to eight. The number of the electrodes 110 is preferably four or more and more preferably six or more.

The electrodes 110 are capacitively coupled to the driver's body faced by the electrodes 110 through the outermost layer of the seat 10 or clothing, and measure electrical signals generated in the human body during cardiac activity as inductive signals generated in the electrodes 110. Thus, by detecting the difference in voltage between the two electrodes 110 of the eight electrodes 110, it is possible to detect the difference in potential between two positions of the body. The electrodes 110 are connected to the ECU 150 via the buffer circuit 115, such as a voltage follower circuit or the like. A voltage signal input from the buffer circuit 115 to the ECU 150 represents the voltage of each of the electrodes 110.

The ADC 120 is provided between the buffer circuit 115 and the MCU 130. The ADC 120 converts the voltage signal input from the buffer circuit 115 to a digital signal through sampling at sufficiently short time intervals, such as a few milliseconds or the like, and outputs the digital signal to the MCU 130.

In the present embodiment, the ADC 120 is always operating and performing outputting to the electrocardiographic data detection apparatus 100. However, an operation of performing conversion for five seconds or longer may be performed intermittently.

The MCU 130 includes an arithmetic unit 130A, a controller 130B, and a communication I/F 130C. The MCU 130 is implemented by a computer that includes a central processing unit (CPU), a random access memory (RAM), a read only memory (ROM), an input/output interface, an internal bus, and the like.

The arithmetic unit 130A includes a difference signal generator 131A, a signal determiner 132A, a difference signal selector 133A, a heartbeat detector 134A, a heartbeat determiner 135A, and an output selector 136A. The signal determiner 132A, the difference signal selector 133A, the heartbeat detector 134A, and the output selector 136A include memories 132A1, 133A1, 134A1, and 136A1, respectively.

The arithmetic unit 130A, the controller 130B, and the communication I/F 130C; and the difference signal generator 131A, the signal determiner 132A, the difference signal selector 133A, the heartbeat detector 134A, the heartbeat determiner 135A, and the output selector 136A in the interior of the arithmetic unit 130A represent functions of programs executed by the MCU 130, as functional blocks. Also, the memories 132A1, 133A1, 134A1, and 136A1 functionally represent a memory of the MCU 130. The MCU 130 may include memories other than those illustrated here, but these memories are omitted in FIG. 1.

<Arithmetic Unit 130A>

In accordance with the voltage value output from the ADC 120, the arithmetic unit 130A is configured to generate heartbeat data, such as R-R intervals and the like, and output the generated heartbeat data to the communication I/F 130C.

The following describes a configuration in which the difference signal selector 133A selects three difference signals upon selecting multiple difference signals suitable for measurement of the heartbeat. However, the number of the multiple difference signals suitable for measurement of the heartbeat is not limited to three. It is preferably half or less the number of the electrodes, and may be, for example, two or four.

Also, the following describes, as an example, a configuration in which when the difference signal selector 133A is to select the difference signal optimum for measurement of the heartbeat from among the multiple difference signals, the difference signal selector 133A selects the difference signal having the highest SN ratio among the multiple difference signals. However, the difference signal selector 133A may select the difference signal optimums for measurement of the heartbeat from among the multiple difference signals using an index other than the SN ratio.

The difference signal generator 131A is configured to select two different voltage values from the eight voltage values output from the ADC 120 within a predetermined time, e.g., five seconds, and calculate a difference signal. Here, there are eight voltage values that are subtrahends, and there are eight voltage values that are minuends. Thus, simply by calculating all difference signals, it is possible to obtain 64 (=8×8) difference signals. However, the difference between the same electrodes is zero, and calculating the difference signal is meaningless in this case. Also, when the subtrahends and the minuends are exchanged, the calculated differences just become to have signs opposite to those before the subtrahends and the minuends are exchanged, and can be regarded as equivalent in terms of electrocardiographic data. Thus, it is meaningless to calculate the difference signals both before and after the subtrahends and the minuends are exchanged. Therefore, in the present embodiment, two different voltages are selected from the eight voltage values, and 28 ($=_8C_2=(8*7)/2$) difference signals are generated. Each of the difference signals is identified by combination of the eight electrodes 110. The difference signal is evaluated in accordance with the ratio of a signal level to a noise level (SN ratio). The difference signal generator 131A outputs the difference signal to the difference signal selector 133A and the signal determiner 132A.

Data that is output from the ADC 120 for five seconds and used for calculation of the difference signal, and data that is output from the ADC 120 for the next five seconds and used for calculation of the difference signal may be continuous data or may be data obtained at a predetermined time interval. Also, for example, data for the first difference signal may be obtained by calculating signals output from the ADC 120 between 0-second point of time and 5-second point of time, and data for the second difference signal may be obtained by calculating signals output from the ADC 120 between 2.5-second point of time and 7.5-second point of time. In other words, the data may be obtained for a partially overlapping period of time (2.5 seconds between 2.5-second point of time and 5.0-second point of time).

The signal determiner 132A is configured to determine suitability for detection of the electrocardiographic data by determining the SN ratios of the 28 difference signals input from the difference signal generator 131A, and output the determination results to the difference signal selector 133A and the output selector 136A. The determination result of the signal determiner 132A represents, as an example, data that is the 28 difference signals arranged in the order of decreasing in the SN ratio; and the electrode numbers corresponding to the SN ratios. A calculation logic for determining the SN ratio in the signal determiner 132A is stored in the memory 132A1, and also the determination result of the signal determiner 132A is stored in the memory 132A1.

The difference signal selector 133A is configured to store, in the memory 133A1, the determination results input from the signal determiner 132A and the 28 difference signals input from the difference signal generator 131A. In accordance with the determination results input from the signal determiner 132A, the difference signal selector 133A selects three difference signals suitable for measurement of the heartbeat from among the 28 difference signals input from the difference signal generator 131A, and outputs them to the heartbeat detector 134A. A selecting method of the three difference signals is stored in the memory 133A1. The selecting method will be described below in detail.

The heartbeat detector 134A is configured to store, in the memory 134A1, the three difference signals input from the difference signal selector 133A. In accordance with each of the difference signals input from the difference signal selector 133A, the heartbeat detector 134A records the point of time at which the heartbeat (beating of the heart) occurs. When the point of time at which the most-recent heartbeat occurs is recorded, the heartbeat detector 134A records a time interval between the current heartbeat and the most-recent heartbeat.

Electrocardiographic data is generated by electrical signals generated in accordance with contraction of the heart's atria, contraction of the heart's ventricles, and the like, and includes the P wave, the QRS wave, the T wave, and the like. The QRS wave is the largest signal among them, and the peak position of the QRS wave is mainly identified as the point of time at which the heartbeat occurs in each of the difference signals. In practice, however, the waveform of the electrocardiographic data measured is different in accordance with the positions of the heart at which the electrodes are attached. Thus, the point of time at which the heartbeat occurs is identified in accordance with the predetermined calculation logic stored in the memory 134A1.

The heartbeat detector 134A outputs the heartbeat data corresponding to the three difference signals, representing the point of time at which the heartbeat occurs or the time interval, to the heartbeat determiner 135A and the output selector 136A. The heartbeat data corresponding to a single difference signal includes multiple data corresponding to the number of heartbeats for five seconds.

When the heartbeat data input from the heartbeat detector 134A is the point of time at which the heartbeat occurs, the heartbeat determiner 135A determines the time interval at which the heartbeat occurs, determines whether or not this time interval is in a range that should be regarded as the heartbeat data, and outputs the determination result to the output selector 136A. When the heartbeat data input from the heartbeat detector 134A is the time interval at which the heartbeat occurs, the heartbeat determiner 135A determines whether or not this time interval is in a range that should be regarded as the heartbeat data, and outputs the determination results to the output selector 136A. In an example of a specific method for determining whether or not the time interval is in the range that should be regarded as the heartbeat data, the time interval is not regarded as the heartbeat data when the time interval has a discontinuous change that is equal to or greater than a threshold.

The output selector 136A is configured to output, to the communication I/F 130C, the heartbeat data that is the most suitable for measurement of the heartbeat among the data that can be regarded as the heartbeat. The heartbeat data that is the most suitable for measurement of the heartbeat is selected in accordance with the three heartbeat data input from the heartbeat detector 134A, the determination results input from the heartbeat determiner 135A, and the SN ratios determined by the signal determiner 132A.

The controller 130B is configured to collectively control: the operations of the difference signal generator 131A, the difference signal selector 133A, the heartbeat detector 134A, and the output selector 136A of the arithmetic unit 130A as descried above; and the operation of the communication I/F 130C. At the timing of generating the next difference signal, the difference signal generator 131A does not generate 28 difference signals, but generates only the three difference signals suitable for measurement of the heartbeat that correspond to the electrode numbers stored in the memory 132A1 of the signal determiner 132A. This is performed as long as data that can be regarded as the heart rate can be obtained by the heartbeat determiner 135A. When the data that can be regarded as the heart rate cannot be obtained, 28 difference signals are generated again. This process is repeated while the electrocardiographic data detection apparatus 100 is activated.

Therefore, compared to generating 28 difference signals each time, the calculation speed can be increased, and the burden on the arithmetic unit and the memory can be suppressed.

The communication I/F 130C is configured to transmit the heartbeat data input from the output selector 136A to the high-level device of the ECU 150 via an on-board network driven by the I/F driver 140.

The heartbeat data is used, for example, to evaluate the driver's tension or stress level, sleepiness, and the like.

<Electrocardiographic Data Detection Method for Comparison and Electrocardiographic Data Detection Method of Embodiment>

Next, the selecting method of the difference signal performed by the difference signal selector 133A will be described. Here, on the assumption that three difference signals are selected, an electrocardiographic data detection method in the electrocardiographic data detection apparatus for comparison and an electrocardiographic data detection method in the present embodiment will be described.

FIGS. 2 and 3 are charts illustrating an example of the SN ratios of the 28 difference signals obtained from the eight electrodes 110.

First, the electrocardiographic data detection method in the electrocardiographic data detection apparatus will be described with reference to FIGS. 2 and 3.

FIG. 2 indicates values that evaluate whether or not a signal indicating the magnitude of the difference between the voltage values of any two electrodes 110 of the eight electrodes 110, i.e., a signal corresponding to an electrocardiographic waveform, is appropriate as an electrocardiographic waveform in accordance with the SN ratio. As described above, a total of 28 ($=_8C_2=(8*7)/2$) difference signals are generated. In FIG. 2, the obtained values are recorded in the upper-right cells.

In FIG. 2, the numbers 1 to 8 as described in the horizontal and vertical directions denote the numbers of the eight electrodes 110. In the following, the difference signal is shown like difference signal (1-7). Difference signal (1-7) is the magnitude of the difference signal between the signal of the electrode 110 of No. 1 and the signal of the electrode 110 of No. 7. The same applies to the electrodes of other numbers. In FIGS. 2 and 3, the first number corresponds to an electrode number in the horizontal direction, and the second number corresponds to an electrode number in the vertical direction. The SN ratio is, as an example, a ratio obtained by using the average value of the voltage values measured over a predetermined time as a denominator (noise level) and the peak value as a numerator (signal level).

The heartbeat data is obtained by obtaining signals of the eight electrodes 110 for five seconds, determining 28 difference signals in the five seconds, and detecting electrocardiographic signals from the difference signals. In the electrocardiographic data detection method for comparison, as an example, difference signals (7-1, 7-2, and 7-4) having the highest, the second highest, and the third highest SN ratios are selected, and the electrocardiographic signal is detected using the selected three difference signals. When the electrocardiographic signal cannot be detected using the three difference signals, the selection is performed again.

A better detection result can be obtained when the electrodes 110 and the human body are closer to each other in a pressurized state via clothing or the outermost layer of a seat. Thus, in the electrocardiographic data detection apparatus for comparison, one of a pair of electrodes (two electrodes 110) that output the original signals of the three difference signals having the best, the second best, and the third best signal qualities is often the electrode 110 that is common in these three difference signals. In FIG. 2, the electrode 110 of No. 7 is the common electrode 110.

Therefore, as a result of movement of the human body, the close state between the common electrode 110 and the human body is changed, and the good measurement state is impaired. In this case, the heartbeat cannot be measured in accordance with the largest, the second largest, and the third largest difference signals. As a result, the following issues arise: i.e., the heartbeat data is not obtainable during the period in which the heartbeat was not measurable; and there is a need to obtain 28 difference signals again and select the largest, the second largest, and the third largest difference signals, thereby increasing the time of the whole measurement.

FIG. 3 is an example illustrating 28 difference signals in a state in which the distance between the electrode 7 and the human body is longer than in the case in which the 28 difference signals as described in FIG. 2 are obtained. The SN ratios of the difference signals (7-1, 7-2, 7-3, 7-4, 7-5, 7-6, and 8-7) of the electrode pairs including the electrode 7 are low. Especially, the SN ratios of the highest, the second highest, and the third highest difference signals (7-1, 7-2, and 7-4) in FIG. 2 are greatly reduced compared to those in FIG. 2.

In this manner, according to the electrocardiographic data detection method for comparison, when the good measurement state with the electrode pair including the common electrode 110 is impaired as a result of movement of the human body, the heartbeat cannot be measured in accordance with the three difference signals.

The electrocardiographic data detection apparatus 100 of the embodiment addresses such issues, and provides the electrocardiographic data detection apparatus and method that can select difference signals suitable for detection of electrocardiographic data from among multiple difference signals.

<Electrocardiographic Data Detection Method of Embodiment>

The difference signal selector 133A selects three difference signals suitable for measurement of the heartbeat from among the 28 difference signals generated by the difference signal generator 131A according to a method as described below. The 28 difference signals are an example of the multiple difference signals and have, for example, the SN ratios as described in FIG. 2.

<Selecting Method of the First Difference Signal>

The difference signal selector 133A selects difference signal (7-1) having the highest SN ratio from among 28 difference signals generated by the difference signal generator 131A. Thus, the difference signal selector 133A selects difference signal (7-1) having the highest SN ratio from among the 28 difference signals, as the first difference signal. Difference signal (7-1) having the highest SN ratio is an example of the first difference signal that is optimum for measurement of the heartbeat. The electrodes 110 of Nos. 1 and 7 that output the two original signals of difference signal (7-1) are an example of the pair of the first electrodes.

<Selecting Method of the Second Difference Signal>

The difference signal selector 133A selects difference signal (5-2) having the highest SN ratio from among 15 difference signals generated from signals of the multiple electrodes 110 (six electrodes of Nos. 2 to 6 and 8) remaining by excluding the pair of the electrodes 110 of Nos. 1 and 7, which output the two original signals of difference signal (7-1), from the 28 electrodes 110. Thus, the difference signal selector 133A selects difference signal (5-2) as the second difference signal. Difference signal (5-2) is an example of the second difference signal that is optimum for measurement of the heartbeat. The electrodes 110 of Nos. 2 and 5 that output the two original signals of difference signal (5-2) are an example of the pair of the second electrodes.

Difference signal (5-2) selected the second in the electrocardiographic data detection method of the embodiment is obtained from the electrodes 110 of Nos. 2 to 6 and 8 excluding the pair of the electrodes 110 of Nos. 1 and 7 related to difference signal (7-1) that was selected the first. Thus, difference signal (5-2) is a difference signal that is not influenced even if the close state between the electrode 110 of No. 1 or 7 and the human body is changed.

In order to achieve the selecting method of the first difference signal and the selecting method of the second difference signal, it is enough that the number of the multiple electrodes 110 is at least four.

<Selecting Method of the Third Difference Signal>

The difference signal selector 133A selects difference signal (4-3) having the highest SN ratio from among the multiple difference signals generated from signals of the multiple electrodes 110 (four electrodes of Nos. 3, 4, 6, and 8) remaining by excluding the electrodes 110 of Nos. 1 and 7, which output the two original signals of difference signal (7-1), and the electrodes 110 of Nos. 2 and 5, which output the original signals of difference signal (5-2), from the 28 electrodes 110. Specifically, difference signal (4-3) having the highest SN ratio is selected from six difference signals ($_4C_2=(4*3)/2=6$). Thus, the difference signal selector 133A selects difference signal (4-3) as the third difference signal. Difference signal (4-3) is an example of the third difference signal that is optimum for measurement of the heartbeat.

Difference signal (4-3) selected the third in the electrocardiographic data detection method of the embodiment is obtained from the four electrodes 110 of Nos. 3, 4, 6, and 8 excluding the electrodes 110 of Nos. 1 and 7, which are related to difference signal (1-7) selected the first, and the electrodes 110 of Nos. 2 and 5, which output the original signals of difference signal (2-5) selected the second. Thus, difference signal (4-3) is a difference signal that is not influenced even if the close state between the electrode 110 of No. 1, 2, 5, or 7 and the human body is changed.

As described above, the electrocardiographic data detection method of the embodiment selects three difference signals suitable for measurement of the heartbeat from among the 28 difference signals. Compared to the method of selecting the three difference signals having the highest, the second highest, and the third highest SN ratios, like in the electrocardiographic data detection method for comparison, it is possible to select difference signals that are not appreciably influenced even if the close state between the eight electrodes 110 and the human body is changed.

In order to achieve the selecting method of the first difference signal, the selecting method of the second difference signal, and the selecting method of the third difference signal, it is enough that the number of the multiple electrodes 110 is at least six.

According to the method of the present embodiment, the SN ratio of the difference signal selected in the case as shown in FIG. 3 is greatly lowered in difference signal (7-1) selected the first, i.e., 2.4, but is not greatly lowered in difference signal (5-2) selected the second, i.e., 4.7, and in difference signal (4-3) selected the third, i.e., 4.0. Thus, detection of the heartbeat is possible, and there is no need to determine difference signals of all electrodes again unlike in the electrocardiographic data detection method for comparison.

<Modified Example of the Selecting Method of the Third Difference Signal>

When selecting a difference signal as the third difference signal, the following method may be used instead of the above-described method.

The difference signal selector 133A identifies the four electrodes 110 of Nos. 1, 2, 5, and 7, i.e., the electrodes 110 of Nos. 1 and 7 that output the original signals of difference signal (7-1) selected the first, and the electrodes 110 of Nos. 2 and 5 that output the original signals of difference signal (5-2) selected the second. Then, the difference signal selector 133A identifies difference signals (1-2, 1-5, 1-7, 2-5, 2-7 and 5-7) obtained from combinations of the two electrodes 110 of the four identified electrodes 110 of Nos. 1, 2, 5, and 7. Further, the difference signal selector 133A selects difference signal (7-4) having the highest SN ratio from among the multiple difference signals remaining by excluding difference signals (2-1, 5-1, 5-2, 7-1, 7-2, and 7-5), which are obtained from combinations of the two electrodes 110 of the four identified electrodes 110 of Nos. 1, 2, 5, and 7, from the 28 difference signals generated by the difference signal generator 131A. Difference signal (7-4) is an example of the third difference signal that is optimum for measurement of the heartbeat.

When selecting the third difference signal, this method excludes a difference between any electrode pair that includes only one of the four electrodes 110 of Nos. 1, 2, 5, and 7, i.e., the electrodes 110 of Nos. 1 and 7 that output the original signals of difference signal (7-1) selected the first, and the electrodes 110 of Nos. 2 and 5 that output the original signals of difference signal (5-2) selected the second. However, such a difference may be included again. Here, an example of the electrode pair including only one of the four electrodes 110 of Nos. 1, 2, 5, and 7 is difference signal (7-4), which includes one of the electrodes 110 of Nos. 1 and 7 that output the original signals of difference signal (7-1) selected the first.

In this modified example, the SN ratio of difference signal (7-4) selected the third in the case as shown in FIG. 3 is 2.4, which is not suitable for detection of the heartbeat. However, it is effective when the close state between the four electrodes 110 of Nos. 1, 2, 5, and 7 and the human body is less changed.

That is, when selecting the third difference signal, the modified example of the selecting method of the third difference signal includes again an electrode pair including only one of the four electrodes 110 of Nos. 1, 2, 5, and 7, i.e., the electrodes 110 of Nos. 1 and 7 that output the original signals of difference signal (7-1) selected the first, and the electrodes 110 of Nos. 2 and 5 that output the original signals of difference signal (5-2) selected the second. Thus, when the close state between the four electrodes 110 of Nos. 1, 2, 5, and 7 and the human body is less changed, a difference signal having a higher SN ratio can be selected.

In order to achieve the selecting method of the first difference signal, the selecting method of the second difference signal, and the modified example of the selecting method of the third difference signal, it is enough that the number of the multiple electrodes 110 is at least five.

<Flowchart>

FIG. 4 is a flowchart illustrating an example of a process executed by the MCU 130 of the electrocardiographic data detection apparatus 100.

When the process is started, the difference signal generator 131A generates difference signals representing differences between the eight voltage values output from the ADC 120 (step S1). The difference signals are transmitted to the difference signal selector 133A and the signal determiner 132A. As an example, it is enough to perform the measurement on the eight electrodes 110 for a predetermined time (e.g., five seconds). If appropriate measurement results cannot be obtained, the measurement may be repeated.

The signal determiner 132A generates determination results representing data that is 28 difference signals input from the difference signal generator 131A, the data being arranged in the order of decreasing in the SN ratio (step S2). The determination results show appropriateness of the 28 difference signals, and difference signals having higher SN ratios are appropriate for measurement of the heartbeat.

The difference signal selector 133A selects three difference signals suitable for measurement of the heartbeat from among the 28 difference signals in accordance with the determination results of the signal determiner 132A (step S3). The three difference signals suitable for measurement of the heartbeat are selected as described with reference to FIG. 2. The selected difference signals are output to the heartbeat detector 134A.

The heartbeat detector 134A detects the heartbeat in accordance with the difference signals input from the difference signal selector 133A (step S4). The heartbeat data representing the detected heartbeat is output to the heartbeat determiner 135A and the output selector 136A.

In accordance with the heartbeat data input from the heartbeat detector 134A, the heartbeat determiner 135A determines appropriateness of the heartbeat data, i.e., whether or not to regard it as heartbeat data, and outputs the determination results to the output selector 136A (step S5).

In accordance with the three heartbeat data input from the heartbeat detector 134A and the determination results input from the heartbeat determiner 135A, the output selector 136A outputs, to the communication I/F 130C, the heartbeat data that is the most suitable for measurement of the heartbeat among the data regarded as the heartbeat data (step S6). When the heartbeat determiner 135 obtains data that is regarded as heartbeat data in the determination performed by the heartbeat determiner 135A, the generation of the difference signal in step S1 is performed only for the electrodes selected by the difference signal selector 133A at the next measurement timing of the heartbeat, followed by proceeding to step S4 with steps S2 and S3 being omitted. The electrodes for which the generation of the difference signal in step S1 is performed may be only the electrodes that output the data determined as the heartbeat data by the difference signal selector 133A and in step S5.

In the present embodiment, the generation of the difference signal in step S1 is performed only for the electrodes selected by the difference signal selector 133A. However, only the electrodes selected by the difference signal selector 133A may be subjected to AD conversion performed by the ADC 120 at the next measurement timing of the heartbeat.

When no data regarded as heartbeat data can be obtained in the determination performed by the heartbeat determiner 135, the process from step S1 is performed at the next measurement timing of the heartbeat.

The heartbeat data may be output to the communication I/F 130C, for example, at a predetermined time interval. The predetermined time interval may be selectable from multiple time intervals.

<Effects>

The electrocardiographic data detection apparatus 100 includes: the multiple electrodes 110 disposed to face the human body; the difference signal generator 131A configured to generate the multiple difference signals from the multiple sets of the multiple electrodes 110 that are each a set of the two electrodes 110 of the multiple electrodes 110, each of the multiple difference signals being generated from signals of the two electrodes 110 of the multiple electrodes 110; and the difference signal selector 133A configured to select the multiple difference signals suitable for measurement of the heartbeat from among the multiple difference signals generated by the difference signal generator 131A. The difference signal selector 133A is configured to select the first difference signal and the second difference signal. The first difference signal is optimum for measurement of the heartbeat among the multiple difference signals generated by the difference signal generator 131A. The second difference signal is optimum for measurement of the heartbeat among the multiple difference signals generated from signals of the multiple electrodes 110 remaining by excluding, from the multiple electrodes 110, the pair of the electrodes 110 that output the original signals of the first difference signal. The second difference signal is obtained from the electrodes 110 remaining by excluding the electrodes 110 related to the first difference signal. Thus, the second difference signal is not appreciably influenced even if the close state between the electrodes 110 related to the first difference signal and the human body is changed.

Therefore, it is possible to provide the electrocardiographic data detection apparatus 100 that can select the difference signals suitable for detection of electrocardiographic data from among the multiple difference signals.

Also, the difference signal selector 133A may select the third difference signal that is optimum for measurement of the heartbeat from among the multiple difference signals generated from the signals of the multiple electrodes 110 remaining by excluding, from the multiple electrodes 110, the pair of the electrodes 110 that output the original signals of the first difference signal and the pair of the electrodes 110 that output the original signals of the second difference signal. The third difference signal is obtained from the electrodes 110 remaining by excluding the four electrodes 110 that output the original signals of the first and second difference signals. Thus, the third difference signal is a difference signal that is not influenced even if the close state between the human body and the four electrodes 110, which output the original signals of the first and second difference signals, is changed. Therefore, it is possible to provide the electrocardiographic data detection apparatus 100 that can select the three difference signals suitable for detection of electrocardiographic data from among the multiple difference signals.

The difference signal selector 133A may select the third difference signal that is optimum for measurement of the heartbeat from among the multiple difference signals remaining by excluding, from the multiple difference signals generated by the difference signal generator 131A, the difference signal obtained from the two electrodes 110 of the four electrodes 110, i.e., the pair of the electrodes 110 that output the original signals of the first difference signal and the pair of the electrodes 110 that output the original signals of the second difference signal. Because the electrode pair including only one of the four electrodes 110 that output the original signals of the first and second difference signals is included again, a difference signal having a higher SN ratio can be selected when the close state between the four electrodes 110 and the human body is less changed. Therefore, it is possible to provide the electrocardiographic data detection apparatus 100 that can select the three difference signals suitable for detection of electrocardiographic data from among the multiple difference signals.

The difference signals suitable for measurement of the heartbeat may be evaluated in terms of the SN ratio. The appropriateness of the difference signal can be readily evaluated in accordance with the SN ratio.

Also, the first difference signal that is optimum for measurement of the heartbeat may be a difference signal having the highest SN ratio among the multiple difference signals generated by the difference signal generator 131A. By selecting, as the first difference signal, the difference signal having the highest SN ratio among all of the multiple difference signals, it is possible to provide the electrocardiographic data detection apparatus 100 that can select the first difference signal suitable for detection of electrocardiographic data from among the multiple difference signals.

Also, the second difference signal that is optimum for measurement of the heartbeat may be a difference signal having the highest SN ratio among the multiple difference signals generated from the signals of the multiple electrodes 110 remaining by excluding, from the multiple electrodes 110, the pair of the electrodes 110 that output the original signals of the first difference signal. By selecting, as the second difference signal, the difference signal having the highest SN ratio among the multiple difference signals generated from the signals of the multiple electrodes 110 remaining by excluding, from all of the multiple electrodes 110, the pair of the electrodes 110 that output the original signals of the first difference signal, it is possible to provide the electrocardiographic data detection apparatus 100 that can readily select the first and second difference signals suitable for detection of electrocardiographic data from among the multiple difference signals.

Also, the third difference signal that is optimum for measurement of the heartbeat may be a difference signal having the highest SN ratio among the multiple difference signals generated from the signals of the remaining multiple electrodes 110. Thus, it is possible to provide the electrocardiographic data detection apparatus 100 that can readily select the third difference signal suitable for detection of electrocardiographic data in accordance with the SN ratios of the multiple difference signals generated from the signals of the remaining multiple electrodes 110.

Also, the third difference signal that is optimum for measurement of the heartbeat may be a difference signal having the highest SN ratio among the remaining multiple difference signals. Thus, it is possible to provide the electrocardiographic data detection apparatus 100 that can readily select the third difference signal suitable for detection of electrocardiographic data in accordance with the SN ratios of the multiple difference signals generated from the signals of the remaining multiple electrodes 110.

The number of the multiple electrodes 110 may be at least five. Thus, it is possible to provide the electrocardiographic data detection apparatus 100 that can select the first and second difference signals suitable for detection of electrocardiographic data from among the multiple difference signals obtained from the signals of the at least five electrodes 110.

The number of the multiple electrodes 110 may be at least seven. Thus, it is possible to provide the electrocardiographic data detection apparatus 100 that can select the first, second, and third difference signals suitable for detection of electrocardiographic data from among the multiple difference signals obtained from the signals of the at least seven electrodes 110.

The electrocardiographic data detection method includes using the electrocardiographic data detection apparatus 100 including: the multiple electrodes 110 disposed to face the human body; the difference signal generator 131A configured to generate the multiple difference signals from the multiple sets of the electrodes 110 that are each a set of the two electrodes 110 of the multiple electrodes 110, each of the multiple difference signals being generated from signals of the two electrodes 110 of the multiple electrodes 110; and the difference signal selector 133A configured to select the multiple difference signals suitable for measurement of the heartbeat from among the multiple difference signals generated by the difference signal generator 131A. The electrocardiographic data detection method includes selecting the first difference signal and the second difference signal by the difference signal selector 133A. The first difference signal is optimum for measurement of the heartbeat among the multiple difference signals generated by the difference signal generator 131A. The second difference signal is optimum for measurement of the heartbeat among the multiple difference signals generated from signals of the multiple electrodes 110 remaining by excluding, from the multiple electrodes 110, the pair of the electrodes 110 that output the original signals of the first difference signal. The second difference signal is obtained from the electrodes 110 remaining by excluding the electrodes 110 related to the first difference signal. Thus, the second difference signal is not influenced even if the close state between the electrodes 110 related to the first difference signal and the human body is changed.

Therefore, it is possible to provide the electrocardiographic data detection method that can select the difference signals suitable for detection of electrocardiographic data from among the multiple difference signals.

In conclusion, it is possible to provide the electrocardiographic data detection apparatus and method that can select the difference signals suitable for detection of electrocardiographic data from among the multiple difference signals.

Although the electrocardiographic data detection apparatus and method of the illustrative embodiments of the present disclosure have been described above, the present disclosure is not limited to the specifically disclosed embodiments, and various changes and modifications are possible without departing from the scope of claims as recited.

What is claimed is:

1. An electrocardiogram apparatus, comprising:
multiple electrodes disposed to face a human body;
a processor; and
a memory storing one or more programs, which when executed, cause the processor to:
generate multiple difference signals from multiple sets of the multiple electrodes that are each a set of two electrodes of the multiple electrodes, each of the multiple difference signals being generated from signals of the two electrodes of the multiple electrodes;

select a first difference signal optimum for measurement of a heartbeat among the generated multiple difference signals;
identify, from the multiple electrodes, a pair of first electrodes that output original signals of the first difference signal;
select a second difference signal optimum for measurement of the heartbeat among the multiple difference signals generated from signals of remaining multiple electrodes in which the pair of first electrodes are excluded; and
cause the multiple electrodes to measure the heartbeat using the second difference signal.

2. The electrocardiogram apparatus according to claim 1, wherein
the one or more programs, when executed, cause the processor to:
select a third difference signal that is optimum for measurement of the heartbeat from among the multiple difference signals generated from signals of the multiple electrodes remaining by excluding, from the multiple electrodes, the pair of the first electrodes that output the original signals of the first difference signal and a pair of second electrodes that output original signals of the second difference signal; and
cause the multiple electrodes to measure the heartbeat using the third difference signal.

3. The electrocardiogram apparatus according to claim 1, wherein
the one or more programs, when executed, cause the processor to:
select a third difference signal that is optimum for measurement of the heartbeat from among the multiple difference signals remaining by excluding, from the generated multiple difference signals, the difference signal obtained from the two electrodes among the four electrodes that are
the pair of the first electrodes that output the original signals of the first difference signal, and
a pair of second electrodes that output original signals of the second difference signal; and
cause the multiple electrodes to measure the heartbeat using the third difference signal.

4. The electrocardiographic data detection apparatus according to claim 1, wherein
the difference signals that are suitable for measurement of the heartbeat are evaluated in accordance with signal-to-noise ratios.

5. The electrocardiographic data detection apparatus according to claim 1, wherein
the first difference signal that is optimum for measurement of the heartbeat is a difference signal having highest signal-to-noise ratio among the generated multiple difference signals.

6. The electrocardiographic data detection apparatus according to claim 1, wherein
the second difference signal that is optimum for measurement of the heartbeat is a difference signal having highest signal-to-noise ratio among the multiple difference signals generated from signals of the multiple electrodes remaining by excluding, from the multiple electrodes, the pair of the first electrodes that output the original signals of the first difference signal.

7. The electrocardiographic data detection apparatus according to claim 2, wherein
the third difference signal that is optimum for measurement of the heartbeat is a difference signal having highest signal-to-noise ratio among the multiple differ-
ence signals generated from signals of the remaining
multiple electrodes.

8. The electrocardiographic data detection apparatus
according to claim 3, wherein the third difference signal that is optimum for measure-
ment of the heartbeat is a difference signal having
highest signal-to-noise ratio among the remaining mul-
tiple difference signals.

9. The electrocardiographic action apparatus according to
claim 1, wherein the multiple electrodes are at least five electrodes.

10. The electrocardiographic action apparatus according
to claim 2, wherein the multiple electrodes are at least seven electrodes.

11. An electrocardiogram method, comprising:

(a) using an electrocardiogram apparatus that includes
multiple electrodes disposed to face a human body,
a processor, and
a memory storing one or more programs, which when
executed, cause the processor to:

generate multiple difference signals from multiple
sets of the multiple electrodes that are each a set
of two electrodes of the multiple electrodes, each
of the multiple difference signals being generated
from signals of the two electrodes of the multiple
electrodes, and (b) selecting a first difference signal, by the processor, the
first difference signal being optimum for measurement
of a heartbeat among the generated multiple difference
signals, identifying, from the multiple electrodes, a pair of first
electrodes that output original signals of the first
difference signal, selecting a second difference signal, by the processor,
the second difference signal being optimum for mea-
surement of the heartbeat among the multiple differ-
ence signals generated from signals of remaining
multiple electrodes in which the pair of first elec-
trodes are excluded, and (c) causing the multiple electrodes to measure the heart-
beat using the second difference signal.

\* \* \* \* \*